United States Patent [19]

Griffith et al.

[11] Patent Number: 4,798,687

[45] Date of Patent: Jan. 17, 1989

[54] 2-AMINO-N-[1,2-DIPHENYL-1-(THI-FLUOROMETHYL)ETHYL]ACETAMIDE DERIVATIVES

[75] Inventors: Ronald C. Griffith, Pittsford; James J. Napier, Rochester, both of N.Y.

[73] Assignee: Pennwalt Corporation, Philadelphia, Pa.

[21] Appl. No.: 11,816

[22] Filed: Feb. 6, 1987

[51] Int. Cl.$^4$ .................................. C07C 103/50
[52] U.S. Cl. ........................ 260/501.1; 260/501.21; 544/168; 546/236; 548/561; 562/561; 564/190; 564/194; 564/196; 564/138
[58] Field of Search ............ 564/194, 195, 190, 196, 564/215; 562/561; 514/362; 260/501.1, 501.21; 544/168; 546/234; 548/561

[56] References Cited

U.S. PATENT DOCUMENTS

| | | | |
|---|---|---|---|
| 2,719,862 | 10/1955 | Bruce et al. | 564/196 |
| 3,950,335 | 4/1976 | Schromm et al. | 564/196 X |
| 4,015,011 | 3/1977 | Schromm et al. | 564/196 X |
| 4,073,941 | 2/1978 | Lindberg et al. | 564/196 X |
| 4,267,374 | 5/1981 | Metcalf et al. | 564/215 X |
| 4,323,704 | 4/1982 | Metcalf et al. | 562/561 |
| 4,536,507 | 8/1985 | Rokaett et al. | 514/362 |
| 4,639,468 | 1/1987 | Roncucci et al. | 564/197 X |

FOREIGN PATENT DOCUMENTS 955508 1/1957 Fed. Rep. of Germany ...... 564/196
343388 2/1960 Switzerland ..................... 564/196

OTHER PUBLICATIONS

CA 64,14162f (Zaheer et al) (1966).
CA 73,25044n (Armando et al) (1970).
CA 77,19586g (Patel et al) (1972).
CA 85,5705y (Hori et al) (1976).
CA 96,19744z (Antoniadou-Vyza et al) (1982).

*Primary Examiner*—Floyd D. Higel
*Attorney, Agent, or Firm*—Elliott Korsen

[57] ABSTRACT

Compounds are provided of the following general structure:

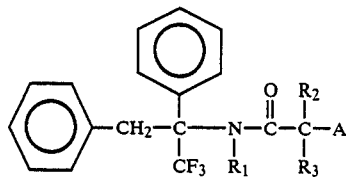

wherein $R_1$, $R_2$ and $R_3$ are independently selected from hydrogen or methyl and A is amino, $C_1$–$C_4$ monoalkylamino, $C_2$–$C_8$ dialkylamino, cyclopropylamino, 1-pyrrolidinyl, 1-piperidinyl or 4-morpholinyl. They are useful for providing sedative and antiepileptic activity.

6 Claims, No Drawings

2-AMINO-N-[1,2-DIPHENYL-1-(THIFLUOROMETHYL)ETHYL]ACETAMIDE DERIVATIVE

SUMMARY OF THE INVENTION

Novel substituted 2-aminoacetamide derivatives have been prepared and found to possess useful sedative and especially antiepileptic activity.

GENERAL DESCRIPTION

This invention relates to novel 2-aminoacetamide compounds of the following general structure (1):

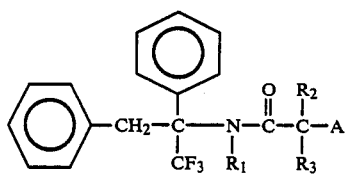
(1)

wherein $R_1$, $R_2$ and $R_3$ are independently selected from hydrogen or methyl and A is amino, $C_1$-$C_4$ monoalkylamino, $C_2$-$C_8$ dialkylamino, cyclopropylamino, 1-pyrrolidinyl, 1-piperidinyl or 4-morpholinyl.

This invention also relates to diastereomeric and optically resolved forms, and to pharmaceutically acceptable acid addition salts of the compounds of general formula (1).

Compounds of this invention possess useful pharmaceutical properties. In particular they possess sedative and antiepileptic properties. Especially useful compounds are those in which $R_1$, $R_2$, and $R_3$ are hydrogen and A is amino.

DETAILED DESCRIPTION

The 2-aminoacetamides of general formula (1) as described fully above are conveniently prepared by suitable amide bond forming reactions from the corresponding amine intermediates of general formula (2):

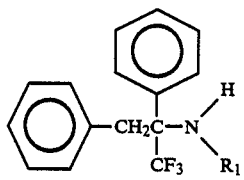
(2)

where $R_1$ is hydrogen or methyl. The preparation of the amines of general formula (2) is described in the "Preparation of Intermediates" Section.

Many amide bond forming reactions may in principle be utilized for the conversion of the amines of general formula (2) to the amides of general formula (1). Two procedures which represent specific methods for this conversion are designated Method A and Method B.

Method A consists of direct coupling of commercially available suitably protected aminoacid derivatives of formula (3):

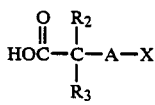
(3)

where $R_2$ and $R_3$, are as described above, A is amino or $C_1$-$C_4$ monoalkylamino and where X is an urethane protecting group preferably benzyloxycarbonyl (CBZ) or t-butyloxycarbonyl (BOC), with an amine of general formula (2), in an inert solvent in the presence of a coupling reagent such as dicyclohexylcarbodiimide with or without 1-hydroxybenzotriazole or other additives to provide coupled products of general formula (4):

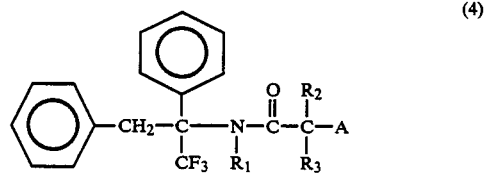
(4)

The protecting groups X, are then readily removed by either catalytic hydrogenation for the CBZ groups or treatment with an acid such as trifluoroacetic or hydrochloric acid for the BOC group to provide the compounds of general formula (1).

Method B consists of reacting an amine of general formula (2) with an activated two carbon acid derivative which contains a leaving group alpha to the carbonyl, such as chloroacetyl chloride, in the presence of an acid acceptor, such as triethylamine, to produce the corresponding 2-chloroacetamide derivative of general formula (5):

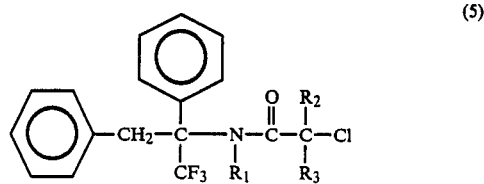
(5)

Such an intermediate can be directly reacted with amines such as ammonia or $C_1$-$C_4$ monoalkylamines, $C_2$-$C_8$ dialkylamines, cyclopropylamine, pyrrolidine, piperidine, or morpholine in solvent such as a lower alkanol, for example methanol or ethanol, or a chlorinated solvent, for example chloroform or methylene chloride or mixtures thereof, to provide the corresponding compounds of general formula (1) where A=amino, $C_1$-$C_4$ monoalkylamino, $C_2$-$C_8$ dialkylamino, cyclopropylamino, 1-pyrrolidinyl, 1-piperidinyl or 4-morpholinyl. In the case of the amines of formula (2) method B is the preferred method of preparation.

The compounds of general formula (1) possess asymmetric centers, and therefore geometric and optical isomers are possible. Such compounds may be conveniently prepared from optically active amines of formula (2) and/or from optically active aminoacid intermediates of formula (3) by the methods described above.

The compounds of general formula (1) are basic compounds and may be used as such or pharmaceutically acceptable acid addition salts may be prepared by treatment with various inorganic or organic acids, such as hydrochloric, hydrobromic, sulfuric, phosphoric, acetic, lactic, succinic, fumaric, malic, maleic, tatraric, citric, benzoic, methanesulfonic or carbonic acids.

The compound of general formula (1) possess useful pharmaceutical properties. In particular they possess useful antiepileptic properties and sedative properties. These activities were assessed by standard methods. Antiepileptic activity was measured by assessing a compounds ability to prevent the hind limb tonic extension component of the seizure in groups of mice induced by maximal electroshock after oral or intraperitoneal administration according to the procedures of the Epilepsy Branch, NINCDS as published by R. J. Porter, et al., *Cleve. Clin. Quarterly* 1984, 51. 293, and compared to the standard agents dilantin and phenobarbital. Activities in the range of 10–400 m/k after oral administration in this assay system were obtained. Sedative activity was assessed by behavioral observation in groups of mice by standard literature procedures. Selected compounds exhibited activity in the range of 30–600 m/k in these assays.

The following non-limiting illustrations and examples are provided to exemplify the preparation of the intermediate amines of formula (2) and their conversion to the novel compounds of general formula (1).

PREPARATION OF INTERMEDIATES

Ilustration 1

Preparation of 3,3,3-Trifluoro-1,2-diphenyl-2-propylamine maleate

To a solution of hexamethyldisilazane (40.1 ml, 0.189 mole) in 200 ml of tetrahydrofuran at 0° under nitrogen was added dropwise n-butyllithium (75.6 ml of 2.5M in hexane, 0.189 mol) and stirred at 5°–10° C. for 30 minutes. This solution was added dropwise over 1 hour to a solution of 2,2,2-trifluoroacetophenone (30.0 g, 0.172 mol) in 200 ml of tetrahydrofuran and stirred for 1.5 hours at 5°–10° C., then treated with a solution of benzyl magnesium chloride (94.5 ml of 2.0M in THF, 0.189 mol) over 45 minutes then allowed to warm to ambient temperature and stirred for 16 hours. The mixture was cooled to 0° C. and 25 ml of saturated ammonium chloride was added and the precipitate removed by filtration through celite. The filtrate was concentrated to 300 ml volume and treated with 300 ml of 1N HCl for 3 hours, then extracted with 2×250 ml of ether. The ether extracts were washed with 100 ml of 1N HCl and the combined aqueous phases were basified with 5% NaOH to pH 10 and extracted with chloroform (3×200 ml). The chloroform extracts were washed with 200 ml brine, dried, and evaporated to give the product as a yellow oil, 38.62 g. Treatment of 5.0 g of the base with maleic acid (2.21 g, 0.019 mol) in 50 ml of methanol and evaporation of the solvent gave a solid which was recrystallized from ether (75 ml) and vacuum dried to give 5.34 g of 3,3,3-trifluoro-1,2-diphenyl-2-propylamine maleate as a white solid, mp 106°–107° C.

Illustration 2

Preparation of N-methyl-3,3,3-trifluoro-1,2-diphenyl-2-propylamine

Acylation of a primary amine with an alkyl chloroformate provides the N-carboalkoxy derivative which can be reduced with lithium aluminum hydride in ether solvents to provide the N-methyl secondary amine. For an example of this process see Horner and Skinner, *Can. J. Chem.*, 1966, 44, 315. Therefore, N-methyl-3,3,3-trifluoro-1,2-diphenyl-2-propylamine may be prepared by reaction of 3,3,3-trifluoro-1,2-diphenyl-2-propylamine with ethyl chloroformate in a two phase mixture of methylene chloride and aqueous sodium carbonate followed by lithium aluminum hydride reduction in tetrahydrofuran of the intermediate N-carboethoxy-3,3,3-trifluoro-1,2-diphenyl-2-propylamine.

Example 1

Preparation of 2-Amino-N-[1,2-diphenyl-1-(trifluoromethyl)ethyl]acetamide maleate To a stirred solution of 1,2-diphenyl-3,3,3-trifluoro-2-propylamine (49.88 g, 0.188 mol) and triethylamine (52.6 ml, 0.376 mol) in 400 ml of methylene chloride at 4° C. under nitrogen, was added dropwise to a solution of chloroacetyl chloride (22.8 ml, 0.282 mol) in 60 ml of methylene chloride. The ice bath was removed and the mixture stirred for 16 hours, cooled at 4° C. and retreated with triethylamine (27 ml) and chloroacetyl chloride (15.2 ml) in 30 ml of methylene chloride, and stirred at ambient temperature for 5 hours. TLC analysis showed that the reaction was still not complete, so the mixture was again cooled to 4° C., 26 ml triethylamine, then a solution of chloroacetyl chloride (15 ml) in methylene chloride (20 ml) added. The mixture was stirred at ambient temperature for 16 hours, then water (200 ml) added and the layers separated. The aqueous phase was extracted with chloroform (2×100 ml) and the combined organic layers were washed with 1N HCl (3×150 ml), dried and evaporated to a dark solid residue. This was treated 10 times with hot cyclohexane, and the combined hexane solutions, decolorized with norite and hot filtered. On cooling an off-white solid crystallized to give 36.9 g of the chloroacetamide, mp 158°–159° C. This material (9.2 g, 0.027 mol) was suspended in 225 ml of ammonia saturated ethanol, and the mixture heated to 78°–85° for 19 hours in a steel bomb. The mixture was cooled to room temperature and the solvent evaporated. The residue was dissolved in water (150 ml), 15% NaOH (50 ml) and chloroform (200 ml), the layers separated, the aqueous layer extracted with chloroform (2×200 ml) and the combined organic phases washed with brine (200 ml), dried and evaporated to a yellow oil, 7.98 g, which crystallized on standing. This was recrystallized from 50 ml of ethyl acetate and 50 ml of cyclohexane to give 3.6 g of white solid. This was dissolved in 30 ml of ethanol, treated with maleic acid (1.29 g, 0.11 mol) and the solution warmed, then treated with ethyl ether (70 ml). Upon cooling a white solid crystallized, which was vacuum dried to give 3.11 g of 2-amino-N-[1,2-diphenyl-1-(trifluoromethyl)ethyl]acetamide maleate, mp 171°–173° C.

Example 2

Preparation of 2-Amino-N-[1,2-diphenyl-1-(trifluoromethyl)ethyl]propanamide tosylate By procedures essentially the same as those described in Example 1 and by substituting 2-chloropropionyl chloride for chloroacetyl chloride; the corresponding 2-amino-N-[1,2-diphenyl-1-(trifluoromethyl)ethyl]propanamide tosylate, mp 161°–185° C., is prepared.

Example 3

Preparation of 2-(Methylamino)-N-[1,2-diphenyl-1-(trifluoromethyl)ethyl]acetamide maleate To a stirred solution of monomethylamine (50 ml, 1.13 mol) in 150 ml of methanol at 0° C. under nitrogen, was added 2-chloro-N-[(1,2-diphenyl-1-(trifluoromethyl)ethyl]acetamide (from Example 1) (10.2 g) followed by 100 ml of methanol to effect solution. The mixture was allowed to slowly warm to ambient temperature and stirred for 24 hours. The solvent was evaporated and the resulting semi-solid was dissolved in 150 ml of chloroform, 100 ml of water and 20 ml of 15% NaOH. The phases were separated, the aqueous phase extracted with chloroform (2×125 ml) and the combined organic phases washed with brine (150 ml), decolorized with charcoal, dried and evaporated to a yellow-orange oil, 9.8 g. This was dissolved in 150 ml of methanol, treated with 3.4 g of maleic acid and the solvent removed under vacuum to yield a solid which was recrystallized from methanol (150 ml) and ethyl acetate (150 ml), then from methanol (30 ml) and ethyl acetate (75 ml) and vacuum dried to give 4.88 g of 2-(methylamino)-N-[1,2-diphenyl-1-(trifluoromethyl)ethyl]acetamide maleate as a white solid, mp 179°–181° C.

By procedures essentially the same as those described above, and by substituting cyclopropylamine for monomethylamine the corresponding 2-(cyclopropylamino)-N-[1,2-diphenyl-1-(trifluoromethyl)ethyl]acetamide may be prepared.

Example 4

Preparation of 2-(Butylamino)-N-[1,2-diphenyl-1-(trifluoromethyl)ethyl]acetamide maleate By procedures essentially the same as those described in Example 3 and by substituting n-butylamine for monomethylamine; the corresponding 2-(butylamino)-N-[1,2-diphenyl-1-(trifluoromethyl)ethyl]acetamide maleate, mp 194°–195° C., is prepared.

Example 5

Preparation of 2-(Dimethylamino)-N[1,2-diphenyl-1-(trifluoromethyl)ethyl]acetamide maleate To a stirred solution of dimethylamine (25 ml, 0.38 mol) in 150 ml of methanol at 0° C. under nitrogen, was added 2-chloro-N-[1,2-diphenyl-1-(trifluoromethyl)ethyl]acetamide (from Example 1) (7.0 g, 0.020 mol). The mixture was allowed to slowly warm to ambient temperature and stirred for 48 hours. The solvent was evaporated and the residue was dissolved in 150 ml of chloroform and 150 ml of water. The aqueous solution was basified to a pH of 10 with 50% NaOH. The phases were separated, the aqueous phase extracted with chloroform (2×75 ml) and the combined organic phases were washed with brine (75 ml), dried and evaporated to a dark oil, 7.2 g. This oil was purified by chromatograhy on a Prep 500 HPLC on silica gel, eluting with 10% ethylacetate/hexane. Pure fractions were combined and evaporated to 4.0 g of an oil. This oil was dissolved in 125 ml of methanol and treated with maleic acid (1.3 g, 0.012 mol) at reflux. The solution was concentrated to a volume of 75 ml. The crystalline salt which formed, was vacuum dried to give 3.61 g of 2-(dimethylamino)-N-[1,2-diphenyl-1-(trifluoromethyl)ethyl]acetamide maleate as a white solid, mp 213°–215° C.

By procedures essentially the same as those described above, and by substituting diethylamine for dimethylamine; the corresponding 2-(diethylamino)-N-[1,2-diphenyl-1-(trifluoromethyl)ethyl]acetamide may be prepared.

Example 6

Preparation of 2-(Azacyclo)-N-[1,2-diphenyl-1-(trifluoromethyl)ethyl]acetamides

By procedures essentially the same as those described in Example 5, and by substituting pyrrolidine, piperidine or morpholine for dimethylamine; the corresponding 2-(1-pyrrolidinyl)-N-[1,2-diphenyl-1-(trifluoromethyl)ethyl]acetamide, 2-(1-piperidinyl)-N-[1,2-diphenyl-1-(trifluoromethyl)ethyl]acetamide or 2-(4-morpholinyl)-N-[1,2-diphenyl-1-(trifluoromethyl)ethyl]acetamide may be respectively prepared.

Example 7

Preparation of 2-Amino-N-methyl-N-[1,2-diphenyl-1-(trifluoromethyl)ethyl]acetamide By procedures essentially the same as those described in Example 1, and by substituting N-methyl-3,3,3-trifluoro-1,2-diphenyl-2-propylamine for 3,3,3-trifluoro-1,2-diphenyl-2-propylamine; the corresponding 2-amino-N-methyl-N-[1,2-diphenyl-1-(trifluoromethyl)ethyl]acetamide may be prepared.

What is claimed:
1. The compound

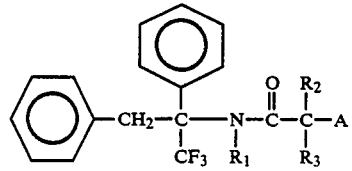

where $R_1$, $R_2$ and $R_3$ are hydrogen or methyl and A is amino, $C_1$–$C_4$ monoalkylamino, $C_2$–$C_8$ dialkylamino, cyclopropylamino, 1-pyrrolidinyl, 1-piperidinyl, or 4-morpholinyl or the pharmaceutically acceptable acid salts thereof.

2. 2-amino-N-[1,2-diphenyl-1-(trifluoromethyl)ethyl]acetamide maleate.

3. 2-amino-N-[1,2-diphenyl-1-(trifluoromethyl)ethyl]propanamide tosylate.

4. 2-(methylamino)-N-[1,2-diphenyl-1-(trifluoromethyl)ethyl]acetamide maleate.

5. 2-(butylamino)-N-[1,2-diphenyl-1-(trifluoromethyl)ethyl]acetamide maleate.

6. 2-(dimethylamino)-N-[1,2-diphenyl-1-(trifluoromethyl)ethyl]acetamide maleate.

* * * * *